(12) United States Patent
Kelly et al.

(10) Patent No.: US 7,714,151 B2
(45) Date of Patent: May 11, 2010

(54) AMINATED ISOFLAVONOID DERIVATIVES AND USES THEREOF

(75) Inventors: Graham Edmund Kelly, Northbridge (AU); Andrew Heaton, Abbotsford (AU); Jane Faragalla, Seven Hills (AU); John Bremner, Balgownie (AU)

(73) Assignee: Novogen Research Pty Ltd, North Ryde NSW (AU)

( * ) Notice: Subject to any disclaimer, the term of this patent is extended or adjusted under 35 U.S.C. 154(b) by 1058 days.

(21) Appl. No.: 10/532,074

(22) PCT Filed: Nov. 3, 2003

(86) PCT No.: PCT/AU03/01446

§ 371 (c)(1),
(2), (4) Date: Nov. 28, 2005

(87) PCT Pub. No.: WO2004/039793

PCT Pub. Date: May 13, 2004

(65) Prior Publication Data

US 2006/0100238 A1 May 11, 2006

(30) Foreign Application Priority Data

Nov. 1, 2002 (AU) ............... 2002952453

(51) Int. Cl.
*C07D 311/02* (2006.01)
(52) U.S. Cl. ..................... 549/404
(58) Field of Classification Search ........... 549/128, 549/404
See application file for complete search history.

(56) References Cited

FOREIGN PATENT DOCUMENTS

| CN | 1093086 | 10/1994 |
|---|---|---|
| WO | WO 9007495 A1 | 7/1990 |
| WO | WO 9218462 A1 | 10/1992 |

OTHER PUBLICATIONS

Inoue, CA 58:33237, abstract only of Sci Repts Tohoku Univ, First Ser., 45(1), pp. 68-72, 1961.*
Donnelly, CA 77:19487, abstract o n ly of Tetrahedron, 28(9), pp. 2545-2551, 1972.*
ramanujam, CA 55:118497, abstract only of Proceedings-Indian Academy of Science, Section a, 48A, pp. 175-179, 1958.*
Lebreton, CA 55:118498, Abstract only of Bull de l'Association Farancaise des Chimiste, vol. 23, pp. 91-125, 1961.*
Inoue, CA 58:33236, abstract only of Sci Repts Tohoku Univ First Ser, 45(1), pp. 63-67, 1961.*
Fukami, CA 54:86477, abstract only of Bull of Ag Chem Soc of Japan, 24, pp. 119-122, 1960.*
Cieslak, CA 54:86476, abstract only of Roczniki Chemii, 30, pp. 825-840, 1956.*
Bradbury, CA 48:28778, abstrract only of J of Chem Soc, pp. 871-876, 1953.*
Inoue, CA 58:33236, abstract only of Sci Repts Tohoku Univ, First Ser., vol. 45(1), pp. 63-67, 1961.*
Chemical Abstract Accession No. 128: 114885 (& Tetrahedron 1998 54(1/2), pp. 233-242, Badia D et al, "A valuable route to benzopyranol [4,3-c]isoquinolines") Compounds with RN 201678-42-4 and 201678-41-3.
Chemical AbstractAccession No. 124:250291 (& Journal of Medicinal Chemistry (1996), 39(8), pp. 1704-1719, Vaccaro W et al,"Inhibitors of Acyl CoA: Cholesterol Acyltransferase") Compounds with RN 175357-71-8 and 175357-72-9.
Chemical Abstract Accession No. 85:21030 ( & Magyar Kemiai Folyoirat (1976), 82(1), pp. 36-39, Szabo V et al, "Synthesis and reactions of isoflavone oxime") Compounds with RN 59564-27-1 and 59564-28-2.
Chemical Abstract Assession No. 77:19487 (& Tetrahedron (1972), 28(9), pp. 2545-2551, Donnelly D.M.X. et al, "cis-3-Methylflavanones") Compounds with RN 36944-54-4.
Chemical Abstract Accession No. 70:11493 ( & Bulletin of the Chemical Society of Japan (1968), 41(9), pp. 2073-2077, Yamaguchi S et al, "Synthesis of trans-isoflavan-4-ols") Compounds with RN 20986-74-7, 20986-75-8, 20986-76-9, 20986-79-2, 20986-80-5, 20986-81-6 and 23642-08-8.
Chemical Abstract Accession No. 70:4085 ( & Bulletin of the Chemical Society of Japan (1986), 41(9), pp. 2078-2082, Inoue N et al, "Rearrangement of isoflavanone oximes with lithium aluminum hydride" Compounds with RN 20991-23-5, 20991-24-6 and 20991-25-7.
Chemical Abstract Accession No. 65:82115 (& Bulletin of the Chemical Society of Japan (1966), 39(7), pp. 1535-1541, Sugimone H et al, Oxygen heterocycles. VIII. Compound with RN 7622-46-0.
Chemical Abstract Accession No. 58:33237 (& Sci. Repts. Tohoku Univ., First Ser. (1961), 45(No. 1), pp. 68-72, Inoue N, "Studies on synthetic isoflavanones. II. Synthesis of isoflavanones from 3-hydroxyisoflavanones") Compounds with RN 97497-17-1, 100322-08-5, 100435-21-0 and 100767-92-8.
Chemical Abstract Accession No. 58:33236 (& Sci. Repts. Tohoku Univ., First Ser. (1961), 45 (No. 1), pp. 63-67, Inoue N, "Studies on synthetic isoflavanones. I. Synthesis of isoflavanones by catalytic hydrogenation of isoflanones") Compounds with RN 59564-27-1, 89286-01-1, 89286-02-2, 89286-03-3, 97724-24-8, 100322-08-5, 100657-54-3, 100733-86-6, 100733-87-7, 100767-92-8 and 100802-67-3.
Chemical Abstract Accession No. 55:118498 ( & Bull. Assoc. franc. chimistes inds. Cuir et doc. Sci. et tech. inds. Cuir (1961), 23, pp. 91-125, Lebreton P, "Leucoanthocyanins") Compounds with RN 122701-70-6.
Chemical Abstract Accession No. 54:86477 ( & Bulletin of the Agricultural Chemical Society of Japan (1960), 24, pp. 119-122, Fukami H et al, "Synthesis of rotenoids. I. Synthesis of chromanochromanone and 2-substituted isoflavanones") Compounds with RN 114863-28-4 and 114863-29-5.

* cited by examiner

*Primary Examiner*—D. Margaret Seaman
(74) *Attorney, Agent, or Firm*—Sughrue Mion, PLLC

(57) ABSTRACT

Aminated isoflavonoid synthesized by aminating the 4-keto group of isoflavanone and isoflavanone ring systems, pharmaceutical compositions containing same and uses thereof as therapeutic agents.

8 Claims, 7 Drawing Sheets

AMINATED ISOFLAVONOID DERIVATIVES AND USES THEREOF

This application is a 371 of PCT/AU2003/001446, filed Nov. 3, 2003; the disclosure of which is incorporated herein by reference.

FIELD OF THE INVENTION

The present invention generally relates to aminated isoflavonoid derivatives based on nitrogen substitution of the 4-keto group of isoflavone and isoflavanone ring systems. The present invention further relates to the synthesis of the aminated isoflavonoid derivatives, compositions containing same and uses thereof as therapeutic agents.

BACKGROUND OF THE INVENTION

Naturally-occurring plant isoflavones are known to possess a wide range of fundamental biological effects on human cells including anti-oxidation and the up-regulation and down-regulation of a wide variety of enzymes and signal transduction mechanisms. Mitotic arrest and cytotoxicity of human cancer cells, increased capillary permeability, increased cellular adhesion, increased response of vascular smooth muscle cells to vaso-relaxants, and agonism of estrogen receptors, are just a few examples of the responses of animal cells to the biological effects of naturally-occurring isoflavonoids.

A range of therapeutic benefits as a result of these biological outcomes have been identified including the treatment and prevention of pre-menopausal symptoms such as pre-menstrual syndrome, endometriosis, uterine fibroids, hyperlipidaemia, cardiovascular disease, menopausal symptoms such as osteoporosis and senile dementia, alcoholism, benign prostatic hypertrophy, and cancers such as prostate, breast and large bowel carcinomas [see WO 93/23069; WO 96/10341; U.S. Pat. No. 5,424,331; JP 62-106017; JP 62-106016; U.S. Pat. No. 5,516,528; JP 62-106016A2; JP 62-106017A2; JP 61-246124; WO 98/50026; WO 99/43335; WO 00/49009; WO 00/644438; WO 99/48496].

While over 700 different naturally occurring isoflavones are described, only a few are confirmed as having potential therapeutic benefits in animals including humans. These include daidzein, genistein, formononetin, biochanin and glycitein. These and all naturally occurring isoflavones are found in nature as the monomeric form either in a free state, or, more likely, bound to a carbohydrate moiety (glycoside). The isoflavone has to be separated from this moiety before it becomes biologically active.

A number of compounds with a structure related to naturally occurring plant isoflavones are also described as having biological properties with potential therapeutic benefit to animals including humans. These include compounds that are naturally occurring metabolites of plant isoflavones produced by bacterial fermentation by gut flora and embrace compounds such as equol and 0-desmethylangolensin [WO 93/23069; WO 98/08503; WO 01/17986; WO 00/66576]. Also included in this group is the synthetic isoflavonoid ipriflavone, which is developed for the treatment of postmenopausal osteoporosis [WO 91/14429] and a wide range of synthetic isoflavonoid analogues [WO 98/08503].

Despite the considerable research and accumulated knowledge in relation to isoflavonoid compounds and derivatives thereof, the full ambit of therapeutically useful isoflavonoid compounds and their activities is yet to be realised. Moreover, there is a continual need for new, improved or at least alternative active agents for the treatment, prophylaxis, amelioration, defence against and/or prevention of various diseases and disorders.

A requirement accordingly exists for new generation compounds that exhibit physiological properties important to the health and well-being of animals, particularly humans, and to find new methods which exploit these properties for the treatment, amelioration and prophylaxis of disease.

SUMMARY OF THE INVENTION

Surprisingly, the present inventors have discovered a new class of molecules based on aminated isoflav-4-one and isoflavan-4-one compounds. In particular the aminated isoflavonoid compounds of the invention relate to imine, hydrazone, semicarbazone, azine, oxime and amine derivatives of isoflav-4-ones and isoflavan-4-ones. The activities of the compounds of the invention are surprising and quite unexpected, even in light of what is presently known about the non-aminated isoflav-4-one and isoflavan-4-one compounds from which these can be derived.

Thus according to an aspect of the present invention there is provided a compound of the general formula (I):

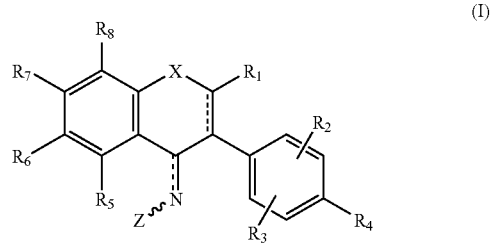

wherein $R_1$, $R_2$, $R_3$, $R_4$, $R_5$, $R_6$, $R_7$ and $R_8$ are independently hydrogen, hydroxy, $OR_9$, $OC(O)H$, $OC(O)R_9$, $OS(O)R_9$, $OSi(R_{10})_3$, $C(O)R_{11}$, $CO_2R_{12}$, alkyl, haloalkyl, aryl, arylalkyl, thio, alkylthio, amino, alkylamino, dialkylamino, nitro or halo, or any two of the substituents $R_2$ $R_3$ and $R_4$ together with the carbon atoms to which they are attached form a cyclic alkyl, cyclic heteroalkyl, aryl or heteroaryl structure, $R_9$ is alkyl, haloalkyl, aryl, arylalkyl or alkylaryl, $R_{10}$ is independently hydrogen, alkyl or aryl, $R_{11}$ is hydrogen, alkyl, aryl, arylalkyl, arylalkyl or an amino acid, and $R_{12}$ is hydrogen, alkyl, haloalkyl, aryl, arylalkyl or alkylaryl, X is O, $NR_{12}$ or S, Z is $R_{13}$, $NR_{14}R_{15}$, $NR_{13}CONR_{14}R_{15}$, $N=CR_{16}R_{17}$ or $OR_{13}$, $R_{13}$, $R_{14}$ and $R_{15}$ are independently hydrogen, amino, thio, nitro, cyano, or optionally substituted alkyl, haloalkyl, acyl, aryl, heteroaryl, arylalkyl or alkylaryl, or the substituents $R_{14}$ and $R_{15}$ together with the nitrogen atom to which they are attached form an optionally substituted cyclic heteroalkyl or heteroaromatic structure, and $R_{16}$ and $R_{17}$ are independently hydrogen, amino, thio, nitro, cyano, or optionally substituted alkyl, haloalkyl, acyl, aryl, heteroaryl, arylalkyl or alkylaryl, or the substituents $R_{16}$ and $R_{17}$ taken together with the carbon atom to which they are attached form an optionally substituted isoflavonoid ring system, or when X is $NR_{12}$, the substituent $R_{12}$ may be a bond such that $R_8$ and X together with the carbon atoms to which they are attached form one of the following structures:

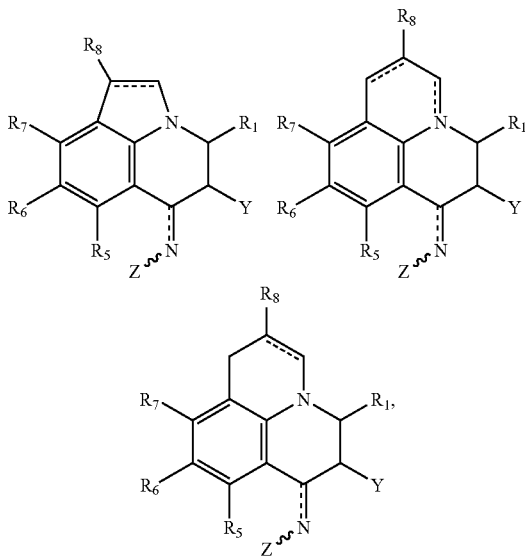

where Y is

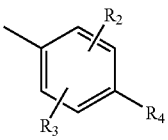

and wherein $R_1$, $R_2$, $R_3$, $R_4$, $R_5$, $R_6$, $R_7$, $R_8$ and Z are as defined above, and the drawing ----- represents either a single bond or a double bond, which compounds include pharmaceutically acceptable salts and derivatives thereof.

According to another aspect of the present invention there is provided a process for the preparation of a compound of formula (I) comprising the step of reacting the 4-keto group of a compound of the formula (X):

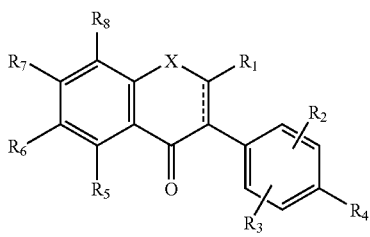

wherein $R_1$, $R_2$, $R_3$, $R_4$, $R_5$, $R_6$, $R_7$, $R_8$ and X are as defined above, and the drawing ----- represents either a single bond or a double bond, with an aminating agent.

It has surprisingly been found by the inventors that the aminated isoflavonoid derivatives of the general formula (I) have particular utility and effectiveness in the regulation of a range of molecular targets in animal cells, and that these molecular targets are intimately involved in signal transduction processes that are fundamental to critical cellular processes such as cell growth, differentiation, migration, and death.

The aminated compounds of the present invention are found to regulate a wide variety of signal transduction processes within animal cells and that these signal transduction processes are involved in a wide range of functions that are vital to the survival and function of all animal cells. Therefore, these compounds have broad-ranging and important health benefits in animals including humans, and in particular have the potential to prevent and treat important and common human diseases, disorders and functions.

The particular benefits of this invention lie in (a) the large range of signal transduction processes targeted by the compounds, (b) the fact that regulation of these various processes includes both up-regulation of some processes and down-regulation of others, and (c) that such a broad and varied effect on signal transduction processes also is accompanied by an independent effect on a range of important enzymes that are fundamental to metabolism and steroidogenesis.

Thus, according to another aspect of the present invention there is provided a method for the treatment, prophylaxis or amelioration of a disease or disorder which method includes the step of administering a therapeutically effective amount of one or more compounds of formula (I) or a pharmaceutically acceptable salt or derivative thereof to a subject.

In particular the present invention provides a method for the treatment, prevention or amelioration of diseases associated with aberrant cell survival, aberrant cell proliferation, abnormal cellular migration, abnormal angiogenesis, abnormal estrogen/androgen balance, dysfunctional or abnormal steroid genesis, degeneration including degenerative changes within blood vessel walls, inflammation, and immunological imbalance, which comprises administering to a subject one or more compounds of the formula (I) or a pharmaceutically acceptable salt or derivative thereof optionally in association with a carrier and/or excipient.

In accordance with another aspect of the present invention there is provided a method of inducing apoptosis in cells expressing abnormal prosurvival phenotype which comprises contacting said cells with one or more compounds of the formula (I) or a pharmaceutically acceptable salt or derivative thereof optionally in association with a carrier or excipient.

In accordance with another aspect of the present invention there is provided a method for inhibiting migration of cells having an abnormal cellular migration phenotype which comprises contacting said cells with a compound of the formula (I) or a pharmaceutically acceptable salt or derivative thereof optionally in association with a carrier or excipient.

In accordance with another aspect of the present invention there is provided a method for inhibiting angiogenesis in tissue expressing aberrant angiogenic phenotype which comprises contacting said tissue with a compound of the formula (I) or a pharmaceutically acceptable salt or derivative thereof optionally in association with a carrier or excipient.

In accordance with another aspect of the present invention there is provided a method for the treatment, prevention or amelioration of cancer in a mammal which method comprises the step of bringing a compound of formula (I) or a pharmaceutically acceptable salt or derivative thereof into contact with cancerous tissue in a mammal that is suffering from a tumour, such that neoplastic development in said cancerous tissue is retarded or arrested.

According to another aspect of the present invention there is provided the use of one or more compounds of formula (I) or a pharmaceutically acceptable salt or derivative thereof in the manufacture of a medicament for the treatment of a disease or disorder.

According to another aspect of the present invention there is provided an agent for the treatment, prophylaxis or amelioration of a disease or disorder which agent comprises one or more compounds of formula (I) or a pharmaceutically acceptable salt or derivative thereof.

According to another aspect of the present invention there is provided a pharmaceutical composition which comprises one or more compounds of formula (I) or a pharmaceutically acceptable salt or derivative thereof in association with one or more pharmaceutical carriers, excipients, auxiliaries and/or diluents.

According to another aspect of the present invention there is provided a drink or food-stuff, which contains one or more compounds of formula (I) or a pharmaceutically acceptable salt or derivative thereof.

In a particularly preferred embodiment the aminated compounds of the present invention exhibit the following therapeutic activities:

1. Direct anticancer function via signal transduction inhibition, cell cycle regulation and apoptosis induction.
2. Prevention of cancer onset and proliferation via COX inhibition
3. Prevention of cancer onset and proliferation via specific 5'alphareductase inhibition
4. Anti-inflammatory effects.

These and other aspects of the invention will become evident from the description and claims which follow, together with the accompanying drawings.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

| | |
|---|---|
| Graph A | Cpd. 1/LNCaP |
| Graph B | Cpd. 1/DU145 |
| Graph C | Cpd. 3/LNCaP |
| Graph D | Cpd. 3/NCI-H460 |

Figure 2:
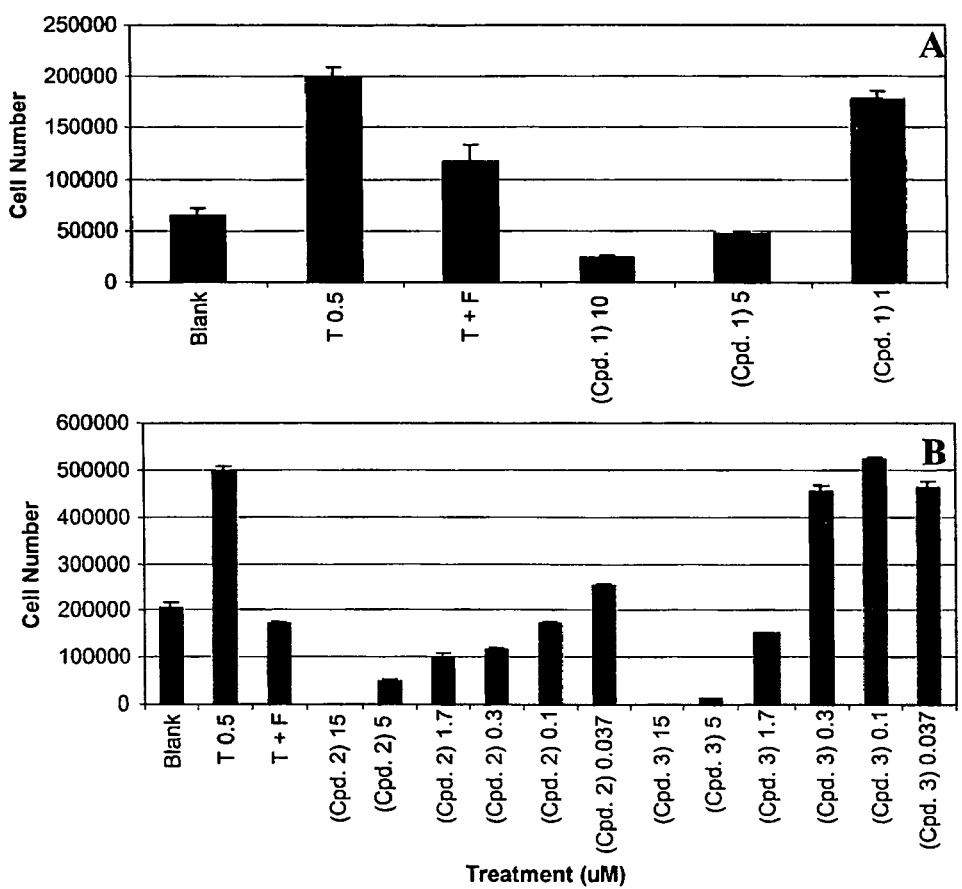

FIG. 2 represents the inhibition of testosterone induced LNCaP proliferation by Cpd. 1 (Graph A), and Cpd. 2 and Cpd. 3 (Graph B).

Figure 3:
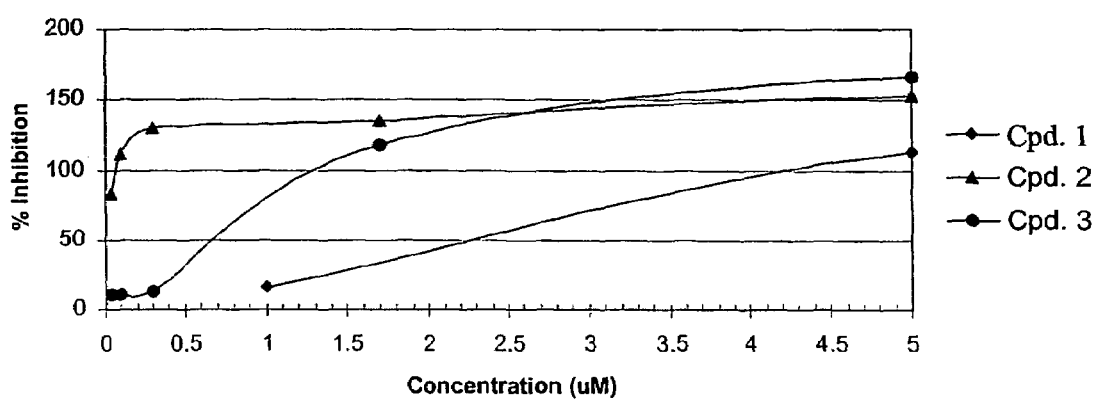

FIG. 3 represents an inhibition profile of testosterone-induced LNCaP proliferation for Cpd. 1, Cpd. 2 and Cpd. 3.

Figure 4:
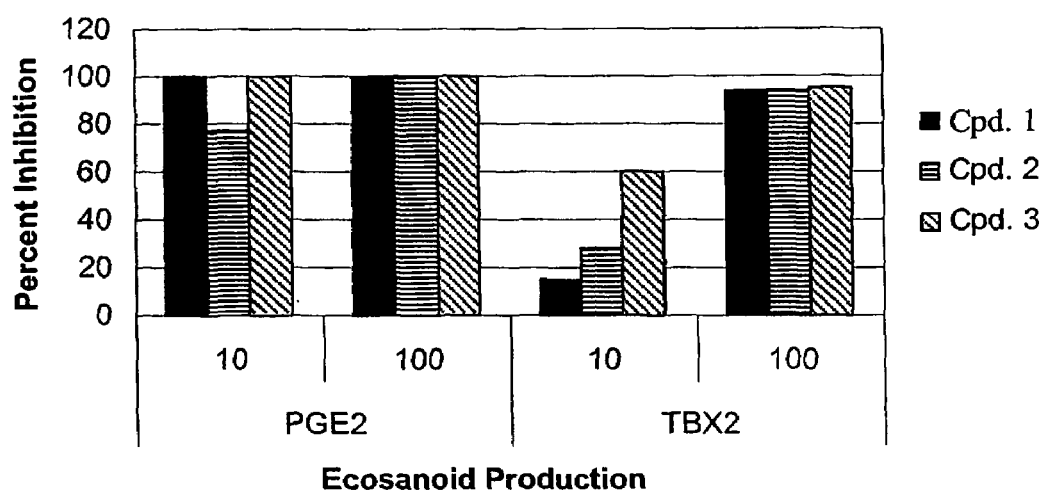

FIG. 4 represents the inhibition of COS (PGE 3) and thromboxane synthase (TBXZ) activity by Cpd. 1, Cpd. 2 and Cpd. 3

Figure 5:
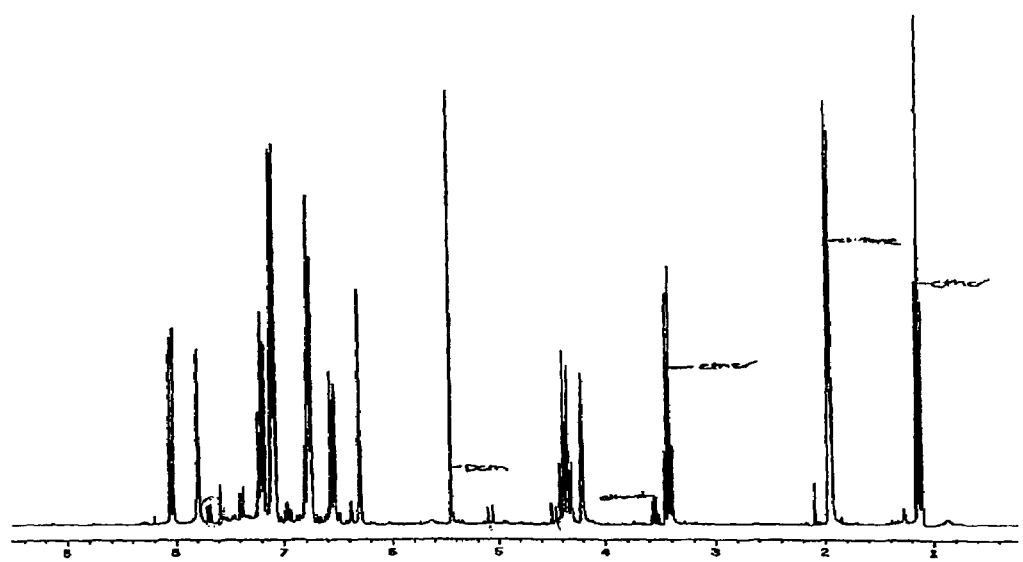

FIG. 5 represents the $^1$H n.m.r. spectrum (d6-acetone) of Cpd. 1.

Figure 6:
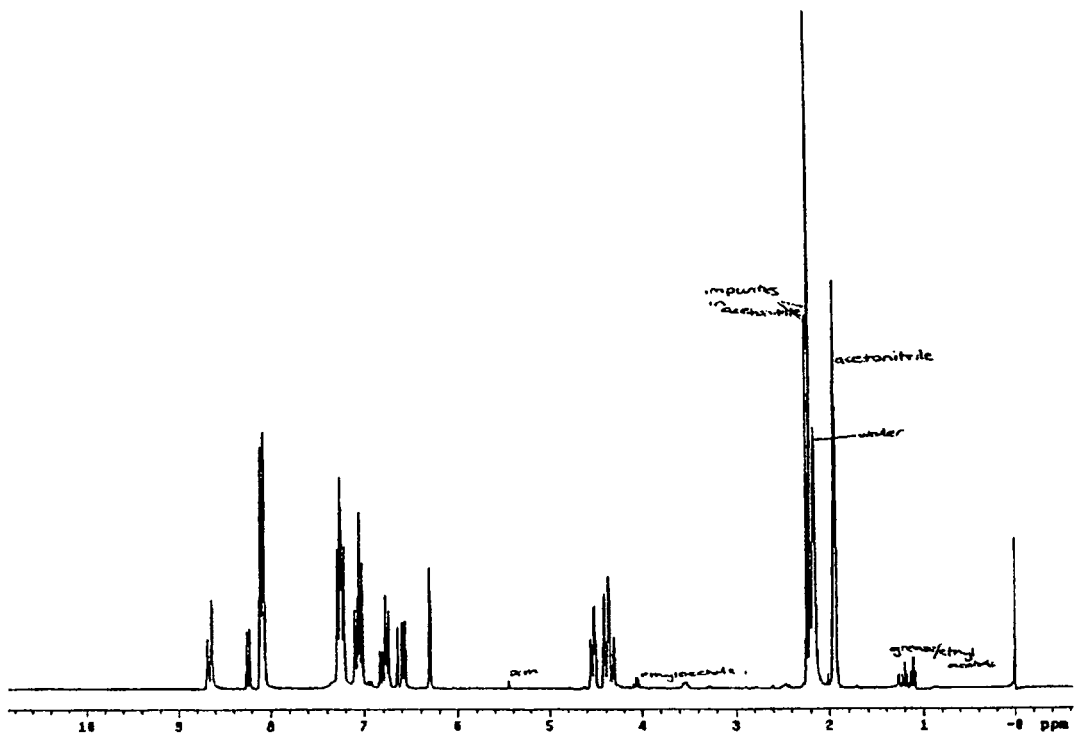

FIG. 6 represents the $^1$H n.m.r. spectrum (d3-acetonitrile) of Cpd. 2.

Figure 7:
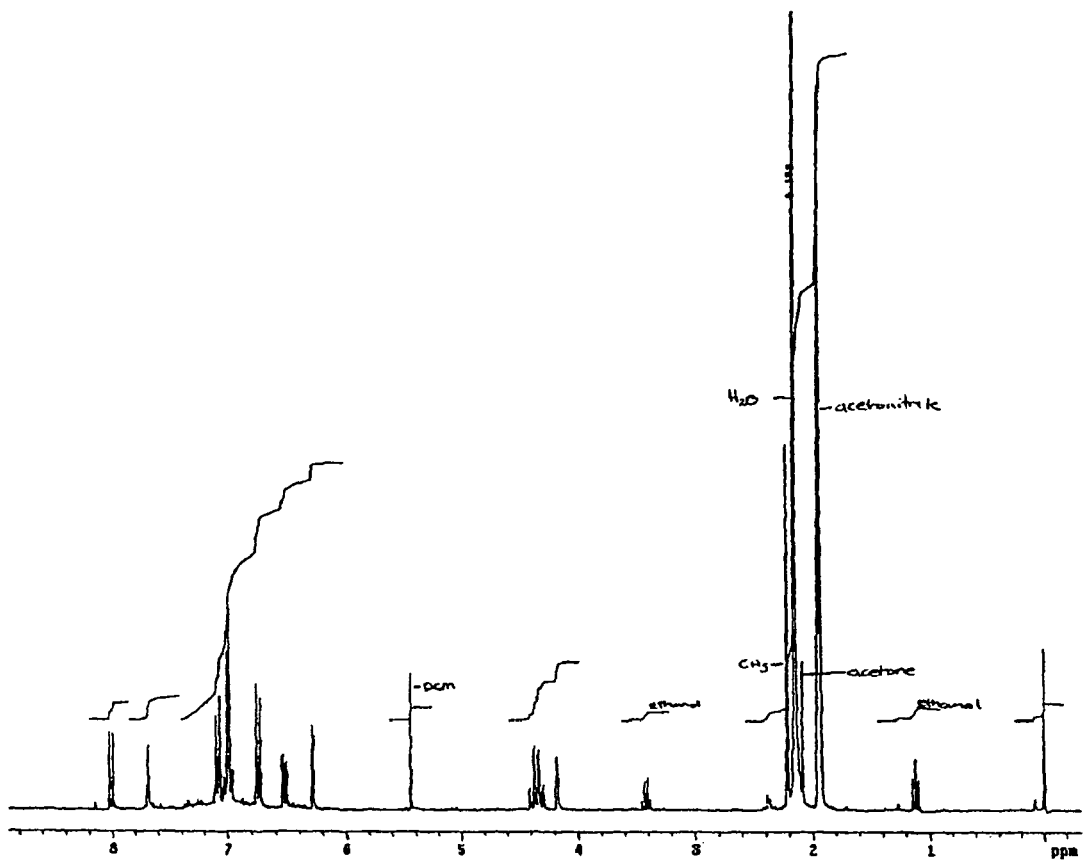

FIG. 7 represents the $^1$H n.m.r. spectrum (d3-acetonitrile) of Cpd. 3.

DETAILED DESCRIPTION OF THE INVENTION

The aminated compounds of the present invention are based on isoflavone compounds and derivatives thereof. The term "isoflavone" as used herein is to be taken broadly to include ring-fused benzopyran molecules having a pendent phenyl group from the pyran ring based on a 1,2-diphenylpropane system. Thus, the classes of compounds generally referred to as isoflavones, isoflavenes, isoflavans, isoflavanones, isoflavanols and the like are generically referred to herein as isoflavones, isoflavone derivatives or isoflavonoid molecules, compounds or derivatives.

The term "alkyl" is taken to include straight chain, branched chain and cyclic (in the case of 5 carbons or greater) saturated alkyl groups of 1 to 10 carbon atoms, preferably from 1 to 6 carbon atoms, such as methyl, ethyl, propyl, isopropyl, butyl, isobutyl, secbutyl, tertiary butyl, pentyl, cyclopentyl, and the like. The alkyl group is more preferably methyl, ethyl, propyl or isopropyl. The alkyl group may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

The term "alkenyl" is taken to include straight chain, branched chain and cyclic (in the case of 5 carbons or greater) hydrocarbons of 2 to 10 carbon atoms, preferably 2 to 6 carbon atoms, with at lease one double bond such as ethenyl, 1-propenyl, 2-propenyl, 1-butenyl, 2-butenyl, 2-methyl-1-propenyl, 2-methyl-2-propenyl, and the like. The alkenyl group is more preferably ethenyl, 1-propenyl or 2-propenyl. The alkenyl groups may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

The term "alkynyl" is taken to include both straight chain and branched chain hydrocarbons of 2 to 10 carbon atoms, preferably 2 to 6 carbon atoms, with at least one triple bond such as ethynyl, 1-propynyl, 2-propynyl, 1-butynyl, 2-butynyl, and the like. The alkynyl group is more preferably ethynyl, 1-propynyl or 2-propynyl. The alkynyl group may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-allyl-carbonyloxy, $C_1$-$C_4$-alkylthio, $C_3$-$C_6$-cycloalkyl or phenyl.

The term "aryl" is taken to include phenyl, biphenyl and naphthyl and may be optionally substituted by one or more $C_1$-$C_4$-alkyl, hydroxy, $C_1$-$C_4$-alkoxy, carbonyl, $C_1$-$C_4$-alkoxycarbonyl, $C_1$-$C_4$-alkylcarbonyloxy, nitro or halo.

The term "heteroaryl" is taken to include five-membered and six-membered rings which include at least one oxygen, sulfur or nitrogen in the ring, which rings may be optionally fused to other aryl or heteroaryl rings including but not limited to furyl, pyridyl, pyrimidyl, thienyl, imidazolyl, tetrazolyl, pyrazinyl, benzofuranyl, benzothiophenyl, quinolyl, isopuinolyl, purinyl, morpholinyl, oxazolyl, thiazolyl, pyrrolyl, xanthinyl, purine, thymine, cytosine, uracil, and isoxazolyl. The heteroaromatic group can be optionally substituted by one or more of fluorine, chlorine, bromine, iodine, carboxyl, nitro, $C_1$-$C_4$-alkoxycarbonyl, $C_1$-$C_4$-alkylaminocarbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl. The heteroaromatic can be partially or totally hydrogenated as desired.

The term "halo" is taken to include fluoro, chloro, bromo and iodo, preferably fluoro and chloro, more preferably fluoro. Reference to for example "haloalkyl" will include monohalogenated, dihalogenated and up to perhalogenated alkyl groups. Preferred haloalkyl groups are trifluoromethyl and pentafluoroethyl.

Optionally substituted groups are those groups where one or more hydrogens have independently been replaced by hydroxy, alkoxy, acyl, thio, aklyl thio, cyano, nitro, amino, alkylamino, dialkylamino, halo or carboxy.

The present inventors have discovered a new class of molecules based on aminated isoflavonoid derivatives. The invention relates to the substitution of the 4-keto group of isoflavone and isoflavanone compounds by nitrogen-based moieties. In particular the aminated isoflavone derivatives relate to imines, hydrazones, semicarbazones, azines and oximes as depicted by the general formulae (II)-(VIII):

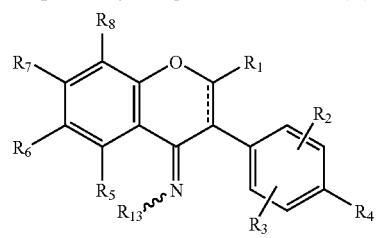
(II)

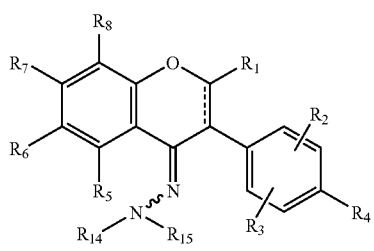
(III)

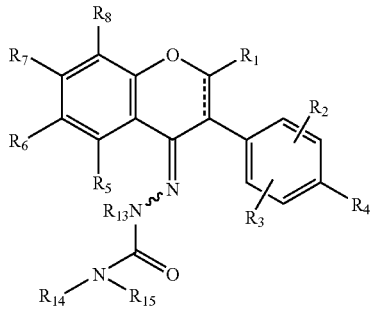
(IV)

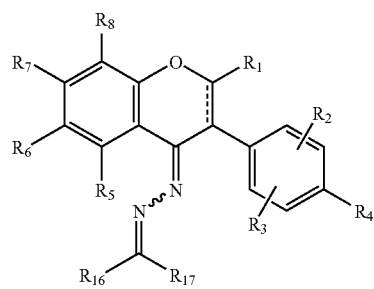
(V)

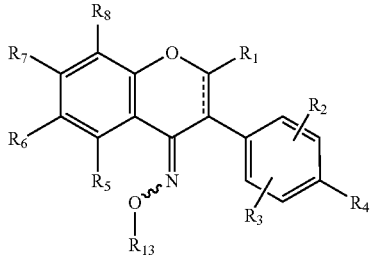
(VI)

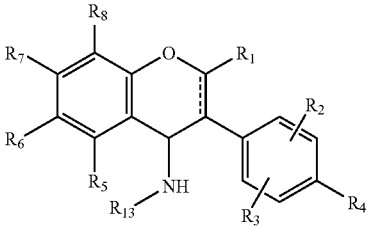
(VII)

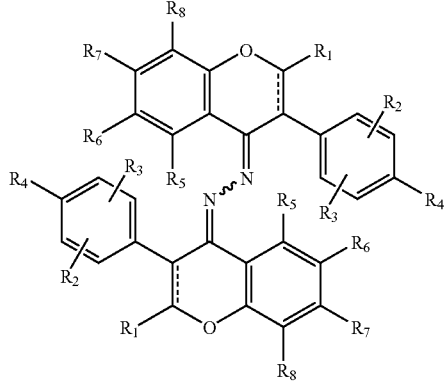
(VIII)

wherein $R_1$, $R_2$, $R_3$, $R_4$, $R_5$, $R_6$, $R_7$ and $R_8$ are independently hydrogen, hydroxy, $OR_9$, $OC(O)R_9$, $OS(O)R_9$, alkyl, aryl, arylalkyl, thio, alkylthio, bromo, chloro or fluoro, $R_9$ is alkyl, fluoroalkyl or arylalkyl, $R_{13}$, $R_{14}$ and $R_{15}$ are independently hydrogen, amino, cyano, thio, nitro, or optionally substituted alkyl, haloalkyl, acyl, aryl, arylalkyl or alkylaryl, or the substituents $R_{14}$ and $R_{15}$ together with the nitrogen atom to which they are attached form an optionally substituted cyclic heteroalkyl or heteroaromatic structure, $R_{16}$ and $R_{17}$ are independently hydrogen, amino, cyano, thio, nitro or optionally substituted alkyl, haloalkyl, acyl, aryl, arylalkyl or alkylaryl, or the substituents $R_{16}$ and $R_{17}$ taken together with the carbon atom to which they are attached form an optionally substituted isoflavonoid ring system, and the drawing ===== represents either a single bond or a double bond;

more preferably they have the following substituents wherein $R_1$ is hydrogen, $R_2$, $R_3$, $R_5$, $R_6$ and $R_9$ are independently hydrogen, hydroxy, $OR_9$, $OC(O)R_9$, alkyl, aryl or arylalkyl, $R_4$ and $R_7$ are independently hydroxy, $OR_9$ or $OC(O)R_9$, $R_9$ is methyl, ethyl, propyl, isopropyl or trifluoromethyl, and $R_{13}$, $R_{14}$ and $R_{15}$ are independently hydrogen, methyl, ethyl, propyl, isopropyl, trifluoromethyl or optionally substituted phenyl, naphthyl or benzyl, or the substituents $R_{14}$ and $R_{15}$ together with the nitrogen atom to which they are attached form an optionally substituted cyclic heteroalkyl or heteroaromatic structure, $R_{16}$ and $R_{17}$ are independently hydrogen, methyl, ethyl, propyl, isopropyl, trifluoromethyl or optionally substituted phenyl, naphthyl or benzyl, or the substituents $R_{16}$ and $R_{17}$ taken together with the carbon atom to which they are attached form an optionally substituted isoflavonoid ring system, and the drawing ---- represents either a single bond or a double bond; and most preferably they have the following substituents wherein $R_1$ is hydrogen, $R_2$, $R_3$, $R_5$, $R_6$ and $R_8$ are independently hydrogen, hydroxy, $OR_9$, $OC(O)R_9$ or methyl, $R_4$ and $R_7$ are independently hydroxy, $OR_9$ or $OC(O)R_9$, $R_9$ is methyl, $R_{13}$ is hydrogen, methyl, ethyl, trifluoromethyl, phenyl, chlorophenyl, nitrophenyl, toluyl, naphthyl, benzyl, chlorobenzyl, nitrobenzyl or methylbenzyl, $R_{14}$ is hydrogen and $R_{15}$ is hydrogen, methyl, ethyl, trifluoromethyl, phenyl, chlorophenyl, nitrophenyl, toluyl, naphthyl, benzyl, chlorobenzyl, nitrobenzyl or methylbenzyl, or the substituents $R_{14}$ and $R_{15}$ together with the nitrogen atom to which they are attached form an optionally substituted cyclic heteroalkyl or heteroaromatic structure, $R_{16}$ and $R_{17}$ are independently hydrogen, methyl, ethyl, trifluoromethyl, phenyl, chlorophenyl, nitrophenyl, toluyl, naphthyl, benzyl, chlorobenzyl, nitrobenzyl or methylbenzyl, or the substituents $R_{16}$ and $R_{17}$ taken together with the carbon atom to which they are attached form an optionally substituted isoflavonoid ring system, and the drawing ---- represents a single bond.

Most preferably the novel aminated isoflavonoid of formula (I) are compounds (1)-(14) as follows:

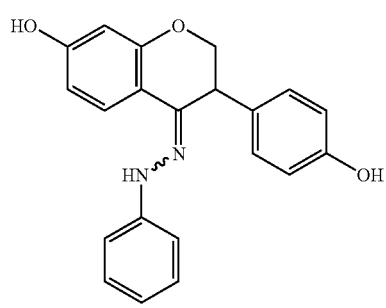

1

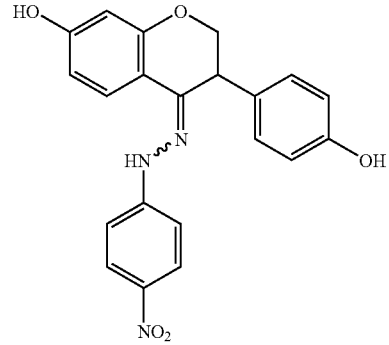

2

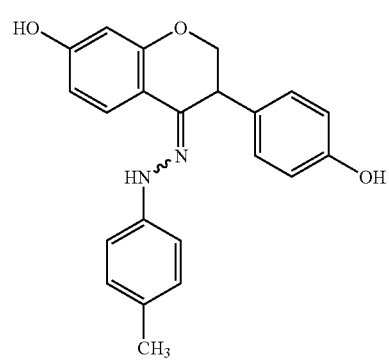

3

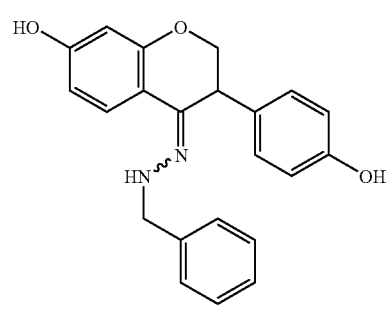

4

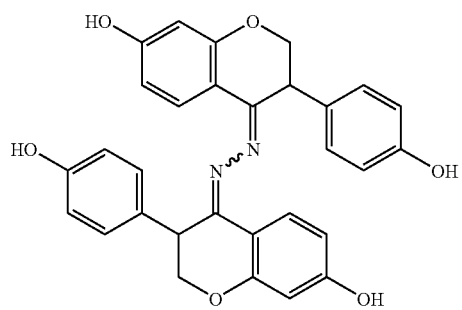

5

-continued

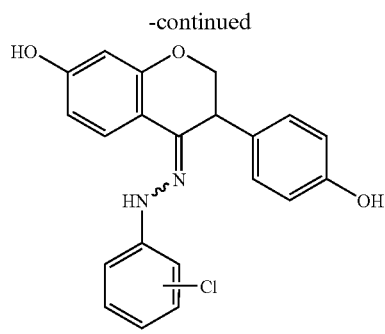

6 o-Cl
7 m-Cl
8 p-Cl

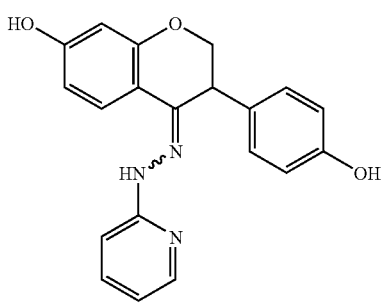
9

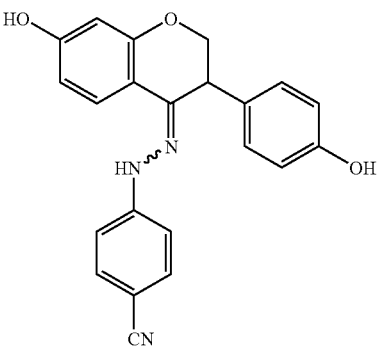
10

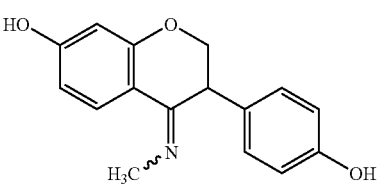
11

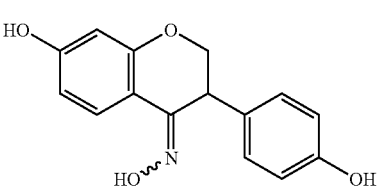
12

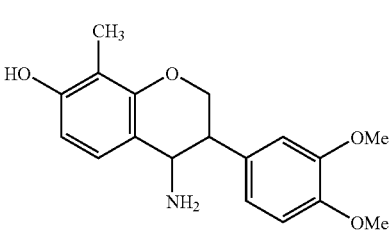
13

-continued

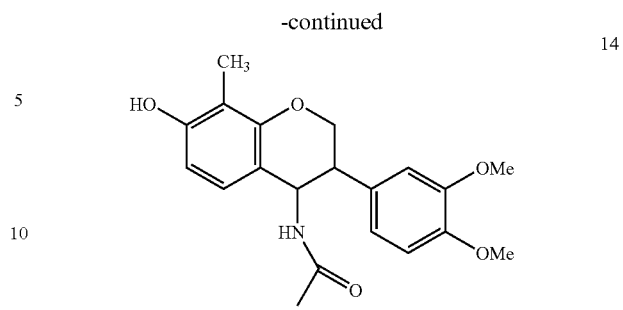
14

The compounds of the invention include all salts, such as acid addition salts, anionic salts and zwitterionic salts, and in particular include pharmaceutically acceptable salts.

Chemical functional group protection, deprotection, synthons and other techniques known to those skilled in the art may be used where appropriate to aid in the synthesis of the compounds of the present invention, and their starting materials.

The preferred compounds of the present invention also include all derivatives with physiologically cleavable leaving groups that can be cleaved ill Vivo from the isoflavone or derivative molecule to which it is attached. The leaving groups include acyl, phosphate, sulfate, sulfonate, and preferably are mono-, di- and per-acyl oxy-substituted compounds, where one or more of the pendant hydroxy groups are protected by an acyl group, preferably an acetyl group. Typically acyloxy substituted isoflavones and derivatives thereof are readily cleavable to the corresponding hydroxy substituted compounds. In addition, the protection of functional groups on the isoflavone compounds and derivatives of the present invention can be carried out by well established methods in the art, for example as described in T. W. Greene, *Protective Groups in Organic Synthesis*, John Wiley & Sons, New York, 1981.

Most preferred isoflavone and isoflavanone starting compounds contemplated for use in accordance with the invention include formnononetin, biochanin, genistein, daidzein and equol, and functional derivatives, equivalents or analogues thereof. Similarly important compounds are the isoflavone metabolites including dihydrodaidzein, cis- and trans-tetrahydrodaidzein and dehydroequol, and derivatives and prodrugs thereof.

Chemical and functional equivalents of a particular isoflavone should be understood as molecules exhibiting any one of more of the functional activities of the isoflavone and may be derived from any source such as being chemically synthesised or identified via screening processes such as natural product screening.

The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, citrate, bicarbonate and carbonate.

The term "pharmaceutically acceptable derivative" or "prodrug" refers to a derivative of the active compound that upon administration to the recipient, is capable of providing directly or indirectly, the parent compound or metabolite, or that exhibits activity itself.

As used herein, the terms "treatment", "prophylaxis" or "prevention", "amelioration" and the like are to be considered in their broadest context. In particular, the term "treatment" does not necessarily imply that an animal is treated until total recovery. Accordingly, "treatment" includes amelioration of the symptoms or severity of a particular condition or preventing or otherwise reducing the risk of developing a particular condition.

The amount of one or more compounds of formula (I) which is required in a therapeutic treatment according to the invention will depend upon a number of factors, which include the specific application, the nature of the particular compound used, the condition being treated, the mode of administration and the condition of the patient. Compounds of formula (I) may be administered in a manner and amount as is conventionally practised. See, for example, Goodman and Gilman, "The pharmacological basis of therapeutics", 7th Edition, (1985). The specific dosage utilised will depend upon the condition being treated, the state of the subject, the route of administration and other well known factors as indicated above. In general, a daily dose per patient may be in the range of 0.1 mg to 5 g; typically from 0.5 mg to 1 g; preferably from 50 mg to 200 mg. The length of dosing may range from a single dose given once every day or two, to twice or thrice daily doses given over the course of from a week to many months to many years as required, depending on the severity of the condition to be treated or alleviated. It will be further understood that for any particular subject, specific dosage regimens should be adjust over time according to the individual need and the professional judgment of the person administering or supervising the administration of the compositions. Relatively short term treatments with the active compounds can be used to cause stabilisation or shrinkage of coronary artery disease lesions that cannot be treated either by angioplasty or surgery. Longer term treatments can be employed to prevent the development of advanced lesions in high-risk patients.

The production of pharmaceutical compositions for the treatment of the therapeutic indications herein described are typically prepared by admixture of the compounds of the invention (for convenience hereafter referred to as the "active compounds") with one or more pharmaceutically or veterinary acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain up to 100% by weight of the active compound, preferably from 0.5% to 59% by weight of the active compound. One or more active compounds may be incorporated in the formulations of the invention, which may be prepared by any of the well known techniques of pharmacy consisting essentially of admixing the components, optionally including one or more accessory ingredients. The preferred concentration of active compound in the drug composition will depend on absorption, distribution, inactivation, and excretion rates of the drug as well as other factors known to those of skill in the art.

The formulations of the invention include those suitable for oral, rectal, ocular, buccal (for example, sublingual), parenteral (for example, subcutaneous, intramuscular, intradermal, or intravenous), transdermal administration including mucosal administration via the nose, mouth, vagina or rectum, and as inhalants, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Formulations suitable for ocular administration include liquids, gels and creams comprising the active compound in an ocularly acceptable carrier or diluent.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and are administered at a rate of 0.1 ml/minute/kg.

Formulations suitable for rectal administration are preferably presented as unit dose suppositories. Formulations suitable for vaginal administration are preferably presented as unit dose pessaries. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vaseline, lanoline, polyethylene glycols, alcohols, and combination of two or more thereof. The active compound is generally present at a concentration of from 0.1% to 5% w/w, more particularly from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound. See for example Brown, L., et al. (1998).

Formulations suitable for transdermal administration may also be delivered by iontophoresis (see, for example, Panchagnula R, et al., 2000) and typically take the form of an optionally buffered aqueous solution of the active compound. Suitable formulations comprise citrate or Bis/Tris buffer (pH 6) or ethanol/water and contain from 0.1 M to 0.2 M active ingredient.

Formulations suitable for inhalation may be delivered as a spray composition in the form of a solution, suspension or emulsion. The inhalation spray composition may further comprise a pharmaceutically acceptable propellant such as carbon dioxide or nitrous oxide.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

Therapeutic methods, uses and compositions may be for administration to humans or animals, including mammals such as companion and domestic animals (such as dogs and cats) and livestock animals (such as cattle, sheep, pigs and goats), birds (such as chickens, turkeys, ducks), marine animals including those in the aquaculture setting (such as fish, crustaceans and shell fish) and the like.

The active compound or pharmaceutically acceptable derivatives prodrugs or salts thereof can also be co-administered with other active materials that do not impair the desired action, or with materials that supplement the desired action, such as antibiotics, antifungals, antiinflammatories, or antiviral compounds. The active agent can comprise two or more isoflavones or derivatives thereof in combination or synergistic mixture. The active compounds can also be administered with lipid lowering agents such as probucol and nicotinic acid; platelet aggregation inhibitors such as aspirin; antithrombotic agents such as coumadin; calcium channel blockers such as verapamil, diltiazem, and nifedipine; angiotensin converting enzyme (ACE) inhibitors such as captopril and enalapril, and β-blockers such as propanolol, terbutalol, and labetalol. The compounds can also be administered in combination with nonsteriodal antiinflammatories such as ibuprofen, indomethacin, aspirin, fenoprofen, mefenamic acid, flufenamic acid and sulindac. The compounds can also be administered with corticosteroids.

The co-administration may be simultaneous or sequential. Simultaneous administration may be effected by the compounds being in the same unit dose, or in individual and discrete unit doses administered at the same or similar time. Sequential administration may be in any order as required and typically will require an ongoing physiological effect of the first or initial active agent to be current when the second or later active agent is administered, especially where a cumulative or synergistic effect is desired.

The isoflavone and isoflavanone compounds for use in the preferred synthetic methods of the present invention may be derived from any number of sources readily identifiable to a person skilled in the art. Preferably, the isoflavones are obtained in the form of concentrates or extracts from plant sources. Again, those skilled in the art will readily be able to identify suitable plant species, however, for example, plants of particular use in the invention include leguminous plants.

More preferably, the isoflavone extract is obtained from chickpea, lentils, beans, red clover or subterranean clover species and the like.

Isoflavone extracts may be prepared by any number of techniques known in the art. For example, suitable isoflavone extracts may be prepared by water/organic solvent extraction from the plant source. It will be appreciated that an isoflavone extract may be prepared from any single tissue of a single species of plant or a combination of two or more different tissues thereof. Similarly, an extract may be prepared from a starting material which contains a heterogeneous mixture of tissues from two or more different species of plant.

Generally, where an isoflavone extract is prepared from plant material, the material may be comminuted or chopped into smaller pieces, partially comminuted or chopped into smaller pieces and contacted with water and an organic solvent, such as a water miscible organic solvent. Alternatively, the plant material is contacted with water and an organic solvent without any pre-treatment. The ratio of water to organic solvent may be generally in the range of 1:10 to 10:1 and may, for example, comprise equal proportions of water and solvent, or from 1% to 30% (v/v) organic solvent. Any organic solvent or a mixture of such solvents may be used. The organic solvent may preferably be a C2-10, more preferably a C1-4 organic solvent (such as methanol, chloroform, ethanol, propanol, propylene glycol, erythrite, butanol, butanediol, acetonitrile, ethylene glycol, ethyl acetate, glycidol, glycerol dihydroxyacetone or acetone). Optionally the water/organic solvent mixture may include an enzyme which cleaves isoflavone glycosides to the aglycone form. The mixture may be vigorously agitated so as to form an emulsion. The temperature of the mix may range, for example, from an ambient temperature to boiling temperature. Exposure time may be between one hour to several weeks. One convenient extraction period is twenty-four hours at 90° C. The extract may be separated from undissolved plant material and the organic solvent removed, such as by distillation, rotary evaporation, or other standard procedures for solvent removal. The resultant extract containing water soluble and non-water soluble components may be dried to give an isoflavone-containing extract, which may be formulated with one or more pharmaceutically acceptable carriers, excipients and/ or auxiliaries according to the invention.

An extract made according to the description provided in the previous paragraphs may contain small amounts of oil which include isoflavones in their aglycone form (referred to herein as isoflavones). This isoflavone enriched oil, may be subject to HPLC to adjust the isoflavone ratios, or, if it is at the desired isoflavone ratio, may be dried, for example in the presence of silica, and be formulated with one or more carriers, excipients and/or auxiliaries to give an isoflavone containing extract. Alternatively, the isoflavones contained in said small amounts of oil may be further concentrated by addition to the oil of a non-water soluble organic solvent such as hexane, heptane, octane acetone or a mixture of one or more of such solvents. One example is 80% hexane, 20% acetone w/w having high solubility for oils but low solubility for isoflavones. The oil readily partitions into the organic solvent, and an enriched isoflavone containing extract falls out of solution. The recovered extract may be dried, for example in an oven at 50° C. to about 120° C., and formulated with one or more pharmaceutically acceptable carriers, excipients and/or auxiliaries.

It will be appreciated that the present invention also contemplates the production of suitable starting isoflavones, functional derivatives, equivalents or analogues thereof, by established synthetic techniques well known in the art. See, for example, Chang et al. (1994) which discloses methods appropriate for the synthesis of various isoflavones as starting materials.

Other suitable methods may be found in, for example, published International Patent Applications WO 98/08503 and WO 00/49009, and references cited therein, which are incorporated herein in their entirety by reference.

Cellular Function

All cellular functions are under the control of a myriad of signals deriving from either distant cells (endocrine signals), neighbouring cells (paracrine signals) or from within the same cell (autocrine signals). These different signals work largely by stimulating the cell's genome (DNA) from where the appropriate cellular response is initiated. The process by which the signal is transmitted to the genome is known as signal transduction. By this we mean pathways, mostly involving different proteins, where activation of one protein catalyses the response of another protein, resulting finally in transcription of a particular gene or set of genes. Homeostasis, by which we mean the integrated functioning of cells, tissues and organs resulting in good health, is the end product of hundreds, possibly thousands, of different signals entering the body's cells on a continuous basis.

From this signalling milieu, it is possible to divide signals arbitrarily into those that are related to a 'specialized function', and those that are related to the fundamental ability of the cell to exist and to function. Examples of 'specialized functions' are pain perception by a nerve cell, production of antibodies by an immune cell, detoxification reactions by a liver cell, or formation of urine by a kidney cell. Examples of 'fundamental functions' are cell survival or cell death, cell proliferation, cell migration, and angiogenesis. It can be seen that the key to regulating whether or not a cell is able to perform 'specialized functions' is regulation of the cell's 'fundamental functions'.

The applicants have found that compounds of the formula (I) regulate many of the 'fundamental functions' of the cell. The following are some examples of the 'fundamental functions' that the inventors have found to be regulated by the aminated compounds of the present invention.

1. Cell Survival/Death

In order to continue to function, including the ability to respond to specialized functions, cells need to be continuously activating pro-survival signal transduction mechanisms. Pro-survival mechanisms act at two main levels—those that actively promote survival and those that actively suppress cell death (apoptosis).

Pro-survival mechanisms involve a number of different signal transduction processes that ultimately cause transcription of certain genes whose end-products promote cell survival. These different processes involve, but are limited to, such molecular targets as MEK, ERK, and NFκB. Phenoxodiol has been found to operate across a range of these processes. One in particular by way of example is the enzyme, sphingosine kinase. Sphingosine kinase phosphorylates the substrate, sphingosine, to sphingosine-1-phosphate. Sphingosine-1-phosphate is an important stimulator of pro-survival mechanisms and is over-expressed in a range of disease states characterized by increased longevity of cells. The aminated isoflavonoid derivatives down-regulate sphingosine kinase activity.

Apoptosis can be achieved by a number of mechanisms as follows:

(a) One such mechanism involves receptors known as 'death receptors'. These include receptors such as Fas/Mort, TGF and TNRF. Activation of receptors normally is suppressed through the production of blocking proteins such as C-flip. The aminated isoflavonoid derivatives have been found to block the production of C-flip, in so doing, promoting the death of cells.

(b) Another mechanism involves the activation of proteolytic enzymes known as caspases. Once activated, these enzymes autolyse the cell. The aminated isoflavonoid derivatives have been found to up-regulate the activity of caspases.

(c) Another mechanism involves disruption of mitochondria leading to the production of various pro-death factors. The aminated isoflavonoid derivatives have been found to promote such disruption through a direct and novel effect on the mitochondria.

It can be seen from the above description, that the aminated isoflavonoid derivatives are able to induce cell death in a comprehensive manner via a number of different pathways. The ability of a single compound to have such broad and complementary effects is novel. But of considerable surprise is the finding that the aminated isoflavonoid derivatives exert such pro-death effects in abnormal cells only.

That is, in normal healthy cells, the aminated isoflavonoid derivatives have no discernible effect on these regulatory processes. Cells that display abnormal activity of these regulatory processes include but are not limited to cells involved in such disease states as cancer, cardiovascular disease, autoimmune diseases, and diseases with immunological, inflammatory or hyperproliferative components.

2. Cell Proliferation

The ability to divide in response to growth signals is another fundamental function required by normal, healthy cells. Sphingosine-1-phosphate appears to play a key role in facilitating the ability of cells to divide. The act of cell division involves a number of different enzymes as follows:

(a) the activation of topoisomerases (I and II) whose task it is to organize DNA prior to mitosis;

(b) the activation of cyclin dependent kinases (CDKs) whose task is it to move the genome through the different stages of mitosis;

(c) inactivation of cyclin dependent kinase inhibitors (CDKIs) whose task it is to inhibit mitosis through suppression of CDKs.

The aminated isoflavonoid derivatives surprisingly inhibit the 3 above enzyme systems, viz. topoisomerase II, CKDs and CDKIs in cells that are behaving abnormally, particularly cells expressing abnormal prosurviving phenotype or aberrant cell proliferation.

3. Cell Migration

It is well understood that the ability of a cell to migrate and to interact with its neighbouring cells is fundamental to health and disease. Sphingosine kinase and matrix-metalloproteases are key regulators of this important cell function. The aminated isoflavonoid derivatives uniquely down-regulate both of these enzyme systems, thus diminishing the ability of cells in a diseased state to migrate.

4. Angiogenesis

The ability to form new blood vessels is well known to be a key event underlying many disease states associated with hyperplasia. Sphingosine kinase is a key facilitator of this event. The aminated isoflavonoid derivatives by down-regulating this enzyme, selectively impair angiogenesis when it occurs in association with disease, and not in healthy tissues.

These broad-ranging effects of the aminated isoflavonoid derivatives on signal transduction mechanisms are complemented surprisingly by inhibitory effects on a wide range of enzymes, such enzymes not normally being regarded as part of signal transduction processes, but of the physiology of the body in more general terms. These effects also include the following:

5. Steroidogenesis

The aminated isoflavonoid derivatives inhibit a number of enzymes involved in steroidogenesis. These include but are not limited to steroid dehydrogenase, 5-α-reductase and aromatase. People skilled in the art would recognize that such effects would have significant impact on the production of steroid hormones including androgens, estrogens and corticosteroids. Such effects would be regarded as someone skilled in the art in having impact on the normal function of the male and female reproductive tissues including the breast, ovary, uterus, endometrium, cervix, vagina, prostate and penis.

In summary, the inventors have surprisingly found that the aminated isoflavonoid derivatives regulate a unique collection of enzymes involved in both general metabolism and physiological function, and in signal transduction pathways that play pivotal roles in cell survival, cell growth, cell differentiation, and cell response to inflammation and immune modulators. Through regulation of this group of enzymes the compounds of the invention have the capacity to (a) to prevent or to treat many forms of disease irrespective of the cause or pathogenesis of that disease, and (b) influence the full range of biological activities of the body's tissues and the way in which disease, age, environmental influences and other drugs influence those activities.

Moreover, it is highly surprising and novel to find that these compounds can cause a human breast cancer cell to undergo apoptosis and die, also can have such diverse effects as antagonising hypertension, redressing the immunological and inflammatory imbalance underlying inflammatory bowel disease, reversing Type 1 diabetes, and reversing male pattern baldness.

It can readily be seen that the aminated isoflavonoid derivatives of the present invention would have particular relevance in the prevention and treatment of various disease states and disorders as follows.

A. Diseases and Disorders Associated with Abnormal Response to Growth Signals, Abnormal Cellular Proliferation, Dysfunctional Apoptosis, and Abnormal Migration Patterns (Metastasis)

These include:
1. all forms of cancer (pre-malignant, benign and malignant) in all tissues of the body. In this regard, the compounds may be used as the sole form of anti-cancer therapy or in combination with other forms of anti-cancer therapy including but not limited to radiotherapy and chemotherapy;
2. papulonodular skin lesions including but not limited to sarcoidosis, angiosarcoma, Kaposi's sarcoma, Fabry's Disease
3. papulosquamous skin lesions including but not limited to psoriasis, Bowen's Disease, and Reiter's Disease;
4. proliferative disorders of bone marrow including but not limited to megaloblastic disease, myelodysplastic syndromes, polycythemia vera, thrombocytosis and myelofibrosis;
5. hyperplastic diseases of the reproductive tract including but not limited to benign prostatic hyperplasia, endometriosis, uterine fibroids, and polycystic ovarian disease.

B. Diseases and Disorders Associated with Abnormal Angiogenesis

These include:
1. diseases and disorders associated with abnormal angiogenesis affecting any tissue within the body including but not limited to metastatic cancers, psoriasis, hemangiomas and telangiectasia.

C. Diseases and Disorders Associated with Abnormal Inflammatory/Immunological Responses These include:
1. diseases and disorders associated with inflammatory reactions of an abnormal or prolonged nature in any of the body's tissues including but not limited to rheumatoid arthritis, tendonitis, inflammatory bowel disease, ulcerative colitis, Crohn's Disease, sclerosing cholangitis;
2. diseases and disorders associated with degenerative changes within the walls of blood vessels including but not limited to the syndrome known commonly as cardiovascular disease (embracing the diseases atherosclerosis, atheroma, coronary artery disease, stroke, myocardial infarction, post-angioplasty restenosis, hypertensive vascular disease, malignant hypertension, thromboangiitis obliterans, fibromuscular dysplasia);
3. diseases and disorders associated with abnormal immunological responses including but limited to dermatomyositis and scleroderma.
4. immunological imbalance including immune deficiency associated with H.I.V. or other viral infective agents or bacterial infective agents, and immune deficiency related to immaturity or aging.

D. Diseases and Disorders Associated with Decreased Cellular Function Including Depressed Response to Growth Signals and Increased Rates of Cell Death These include:
1. actinic damage characterized by degenerative changes in the skin including but not limited to solar keratosis, photosensitivity diseases, and wrinkling;
2. autoimmune disease characterized by abnormal immunological responses including but not limited to multiple sclerosis, Type 1 diabetes, systemic lupus erythematosis, and biliary cirrhosis;
3. neurodegenerative diseases and disorders characterized by degenerative changes in the structure of the neurological system including but not limited to Parkinson's Disease, Alzheimer's Disease, muscular dystrophy, Lou-Gehrig Disease, motorneurone disease;
4. diseases and disorders associated with degenerative changes within the eye including but not limited to cataracts, macular degeneration, retinal atrophy.

E. Diseases and Disorders Associated with Dysfunctional or Abnormal Steroidogenesis and Function of Reproductive Hormones These include:
1. conditions in women associated with abnormal estrogen/androgen balance including but not limited to cyclical mastalgia, acne, dysmenorrhoea, uterine fibroids, endometriosis, ovarian cysts, premenstrual syndrome, acute menopause symptoms, osteoporosis, senile dementia, infertility;
2. conditions in men associated with abnormal estrogen/androgen balance including but not limited to benign prostatic hypertrophy, infertility, gynecomastia, alopecia hereditaria and various other forms of baldness.

The physiological effects ascribed to the aminated isoflavonoid derivatives of the invention particularly relate to the general areas of signal transduction pathways, anti-cancer applications, anti-inflammatory activity and as cardio-protective agents. More particularly the aminated isoflavonoid derivatives of the invention show broad therapeutic indications including, and in particular, anti-cancer activity via signal transduction inhibition, cell cycle regulation and apoptosis induction, antiangiogenesis (MMP inhibition), signal transduction perturbation (receptor protein tyrosine kinase inhibitor), COX inhibition, 5'-alpha reductase inhibition, cardio protective properties and anti-inflammatory effects.

Specific areas of utility of the compounds of the present invention are described and exemplified as follows:

Anti-Cancer:

In many western countries prostatic adenocarcinoma, secondary to lung cancer, is the most commonly diagnosed malignancy in men and the most common cause of death (Landis et al., 1999; Hsing et al., 2000). Established treatment options for localized prostate cancer, including surgery (radical prostatectomy) and radiation therapy, are curative in only 52-78% of cases with the remaining proportion of cases suffering relapse due to residual disease (Morris and Scher, 2000; Papatsoris and Papavassiliou, 2001). While androgens have an important role in controlling the growth of the normal prostate gland, they also promote onset of benign prostatic hyperplasia (BPH) and prostate cancer progression by trans-activating cellular proliferation genes facilitate via the ligand bound androgen receptor (AR) (Amanatullah et al., 2000). Hence in early disease the mainstay of primary treatment options is androgen ablation therapy utilising both surgical and/or pharmaco-therapeutic methods (Papatsoris and Papavassiliou, 2001).

Interestingly epidemiological studies on the prevalence of prostate cancer in eunuchs, who have a deficiency in 5'alphareductase, show that this subset of the population have a very low incidence of the disease. In the androgen-signaling cascade 5'AR is responsible for the conversion of testosterone to dihydrotestosterone which, in comparison with testosterone, has a much stronger binding affinity for the AR and is able to elicit a stronger proliferative response (Papatsoris and Papavassiliou, 2001). As such considerable research effort has focused on defining novel 5'AR inhibitors. There are two isoforms of NADPH-dependent 5'alphareductase, termed types I and II, with type I expressed primarily in human scalp, skin and liver, and type II expressed primarily in the prostate. Finasteride, a type II specific inhibitor, is the only available SAR inhibitor to treat BPH, and early phase prostate cancer when used in combination with an anti-androgen (such as megestrol acetate). However, given the steroidal structure of finasteride and potential adverse effects, considerable research has focused on elucidating other nonsteroidal inhibitors of 5'alpha-reductase that are clinically acceptable (Chen, et al., 2001).

Recent evidence infers that cancer initiation and progression may be facilitated via the excess production of prostaglandens in inflamed tissue (Vainio, 2001). Cyclooxygenases (COX) catalyse the conversion of arachidonic acid (AA) to prostaglandins and thromboxanes. Supporting epidemiological studies in conjunction with laboratory studies provide strong evidence to suggest that traditional nonsteroidal anti-inflammatory drugs (NSAIDs including aspirin) and COX-2 inhibitors (celecoxib) may reduce the risk of colon cancer (Koki et al., 2002). Indeed clinical biopsies from many different malignancies consistently show a significant over-expression of COX-2. The presumed anti-cancer mechanism of action elicited by NSAIDs is thought to be due to their ability to inhibit the production of prostaglandins via COX-2, which can drive angiogenesis and prevent apoptosis of cancer cells (Vaino, 2001; Fosslien, 2001.)

Anti-Inflammatory:

Prostaglandins such as $PGE_2$ and $PGI_2$ and thromboxanes (TXs) such as $TXA_2$ are fatty acid derivatives known as eicosanoids (Penglis et al. 2000). They are involved in both normal physiology and inflammatory responses. AA released from membrane phospholipids, is the primary substrate for COX enzymes thus giving rise to eicosanoids. Regardless of the COX isotype (COX 1 and COX 2) prostaglandin ($PGH_2$) is the main intermediate of this reaction and it is the common precursor for downstream prostanoid production ($PGE_2$, $PGI_2$ and $TXA_2$)). The potential of a test agent to demonstrate anti-inflammatory activity can be assessed by measuring the compound's ability to inhibit PG and TX synthesis in screening assays. The preliminary data presented in the Examples which follow on the aminated isoflavones of the invention and their ability to inhibit both thromboxane synthase and COX support that this class of molecule has therapeutic application as an NSAID.

The invention is further illustrated by the following non-limiting Examples and accompanying drawings.

Example 1

General Synthetic Methods

1. Imine Synthesis

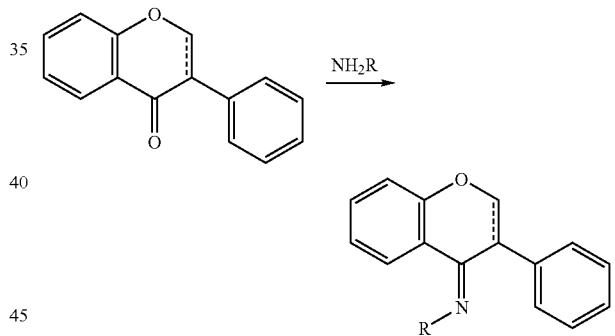

2. Hydrazone Synthesis

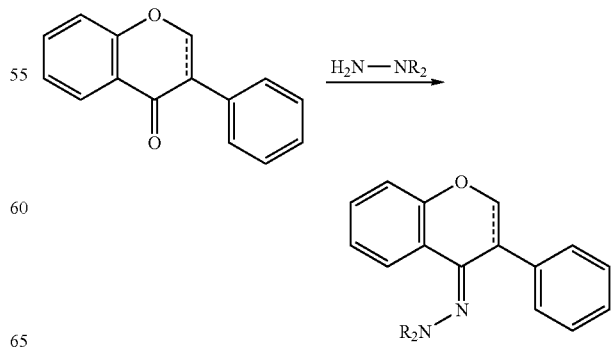

3. Semicarbizone Synthesis

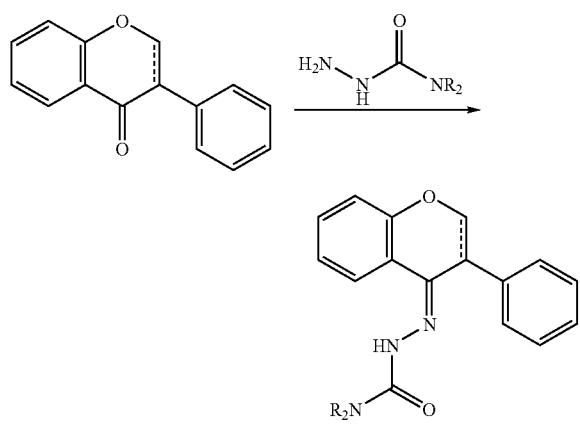

4. Azine Synthesis

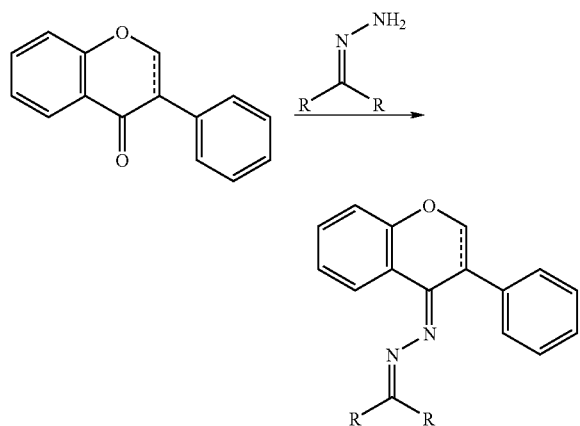

4.1 Azine Dimer Synthesis

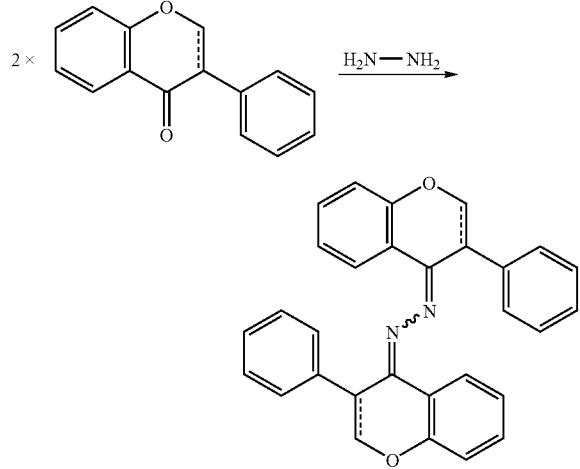

5. Oxime Synthesis

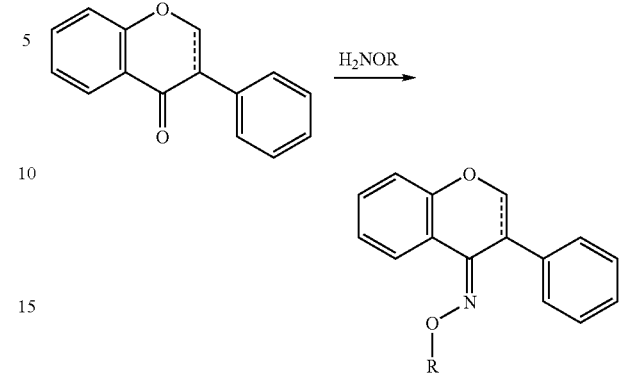

6. Amine Synthesis (Reductive)

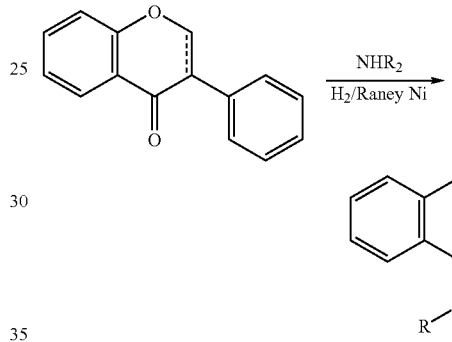

In the above general methods, the structures may be optionally substituted with the desired substituents, or synthons or derivatives thereof. The reactive amine compounds may be present as, for example, their hydrochloride salts and the reactions performed in the presence of a base such as sodium acetate, or as appropriate as determined by a skilled synthetic chemist.

Synthesis

Dihydrodaidzein (1 mmol) was refluxed with 3 mole equivalents of the phenylhydrazine hydrochloride and 3 mole equivalents of sodium acetate (246 mmol) in 4 ml of methanol for 6 hours.

The solution was filtered and the methanol removed under reduced pressure. The product was then purified by silica gel column chromatography (10% ether, 90% dichloromethane), yielding between 40% and 60% of the product.

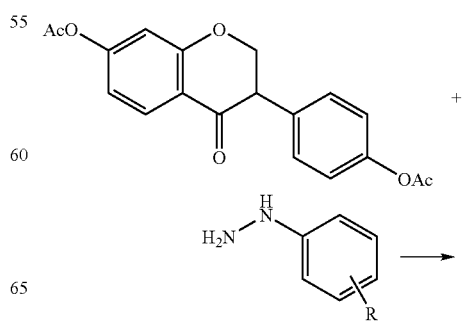

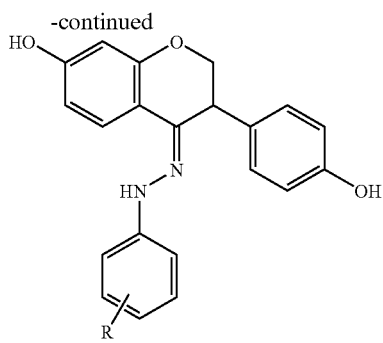

Cpd. 1 R = H
Cpd. 2 R = p-NO₂
Cpd. 3 R = p-CH₃

R=H

H-NMR: (d6-acetone) 8.046 (s), 8.018 (s), 7.787 (s), 7.194 (t), 7.088 (d), 6.762 (m), 6.542 (d of d), 6.292 (d), 4.400 (d of d), 4.3165 (d of d), 4.198 (s) CI-MS (+): 256

R=p-NO₂

H-NMR: (d3-acetonitrile) 8.685 (s), 8.638 (s), 8.239 (d), 8.079 (d), 7.247 (t), 7.046 (m), 6.817 (d of d), 6.60 (d), 6.646 (d), 6.583 (d of d), 4.546 (d), 4.392 (d), 4.309 (s) CI-MS (+): 298

R=p-CH₃

H-NMR: (d3-acetonitrile) 8.028 (s), 7.999 (s), 7.689 (s), 7.085 (d), 7.000 (d), 6.45 (d), 6.529 (d of d), 6.285 (d), 4.388 (d of d), 4.321 (d of d), 4.180 (s), 2.220 (s) CI-MS(+): 361, 344, 256

In a similar way, the benzyl substituted compound 4, chloro phenyl substituted compounds 6-8, pyrido compound 9 and cyano compound 10 were also prepared.

The dimeric compound 5 was prepared by standard azine synthesis.

Reaction of dihydrodaidzein (1 mmol) with methylamine (3 mmol) afforded the methyl imine compound 11. In a similar way the hydroxy imine 12 was also prepared with hydroxylamine.

Acylation of the amino derivative 13 from the reductive amination (ammonia/H₂/Raney Ni) with 3 eq. acetic anhydride and mild acid work-up gave the N-acetyl derivative 14 in near quantitative yield.

Example 2

Methods

Cell Cytotoxicity Analysis:

The method of Alley et al. (1988) was followed. Briefly, prior to cytotoxicity screening a growth curve was constructed for each tumour line to be screened to determine growth kinetics, optimal seeding density to yield logarithmic growth over five days, and the corresponding lag time. Spent culture medium was aspirated from a sub-confluent adherent monolayer culture (T-75), the cells trypsinised and resuspended in a minimal volume of culture medium. After counting cells, a 96-well plate was seeded at an appropriate density (100 μl) to yield optimal growth parameters and the plate was then incubated at 37° C. under 5% CO2. After the pre-determined lag-time the plate was treated with either vehicle (negative control) or serial dilutions of the test compound prepared in culture medium, and then incubated for a further five days. MTT (0.5 mg/ml) prepared in PBS was added to all wells and incubated at 37° C. for ~3 hr. Spent medium was then carefully aspirated and DMSO (150 μt) was added to solubilise cells and the reduced formazan. Absorbance was then read on a SpectraMax plate reader at 570 nm and viable cells in treated plates were expressed as a percentage of cells in control plates.

Androgen Inhibition Studies:

The method of Negri-Cesi and Motta (1994) and Negri-Cesi et al. (1999) was followed. Briefly, LNCaP cells were cultured in RPMI supplemented with 10% fetal calf serum and 2 mM L-glutamine at 37° C. under 5% CO₂. At day 0 a subconfluent LNCaP culture flask (80%) were harvested by trypsinisation, washed, resuspended in RPMI media completed with charcoal stripped fetal calf serum (RPMIi) and seeded into 12 well plates at 30,000 cells per well (15,000 cells/mL). The plates were cultured at 37° C. with 5% CO₂ for 48 hours. On day 2, spent media was carefully aspirated from all plates and then replenished with 2 ml RPMIi containing either testosterone (0.5 pM) as positive control, testosterone plus finasteride (1 uM) as inhibitor control and vehicle as growth control (equivalent concentration of DMSO). Test plates were treated as described above; only serial dilutions of test compounds prepared in RPMIi were used. Concentrations of test compound were chosen based on their cytotoxicity profile as determined in the cell cytotoxicity analysis methods section above i.e. the top concentration used in the LNCaP proliferation assay was determined as the concentration at which cells first appear close to 100% viable along the cytotoxicity curve. This concentration was chosen to ensure that any inhibition of proliferation imparted by the test agent was due to the inhibition of 5'AR and not due to direct killing of the cells. It is important not to disturb cell monolayer during the addition of treatments. On days 5 and 8 the process followed on day 2 was repeated for all plates. On day 11 spent media was aspirated from all wells, cells were washed gently with PBS (500 μl), trypsinised and the cells in each well counted using a haemocytometer. The average cell count and standard deviation was calculated and the result expressed as the % inhibition of testosterone-induced proliferation in comparison with vehicle control.

Thromboxane Synthase and COX Inhibition Screening Assays:

Human buffy coats were obtained from the Red Cross Blood Bank. Buffy coat (50 ml) was diluted 1:2 with sterile phosphate buffered saline (PBS), overlayed onto Lymphoprep density gradient medium and centrifuged at 800 g for 20 min. The mononuclear cell (MNC) layer was removed and washed with PBS and monocyte enriched cells were prepared from MNC by counter-current centrifugal elutriation. Monocytes were then resuspended in RPMI tissue culture medium with 10% foetal calf serum at $1.5 \times 10^6$ cells/ml. Test analogues were prepared in DMSO and incubated with monocytes at 37° for 30 min at either 10 or 100 μM. After the 30 min pre-incubation, bacterial lipopolysaccharide (LPS) was added (200 ng/ml) and cells were incubated for a further 18 h at 37° in 5% CO2. After centrifugation, cell-free supernatants were then removed and assayed for either prostaglandin or thromboxane production, as determined by radioimmunoassay. Because TXA₂ is labile in aqueous medium, TXB₂, the stable hydrolysis product of TXA₂, was measured. For each dose (0, 10, 100 μM), incubations were performed in triplicate. Results are expressed as mean±SD, n=3. ANOVA followed by Newman-Keuls multiple comparisons test was used to examine differences between doses and the control values.

Figure 1:
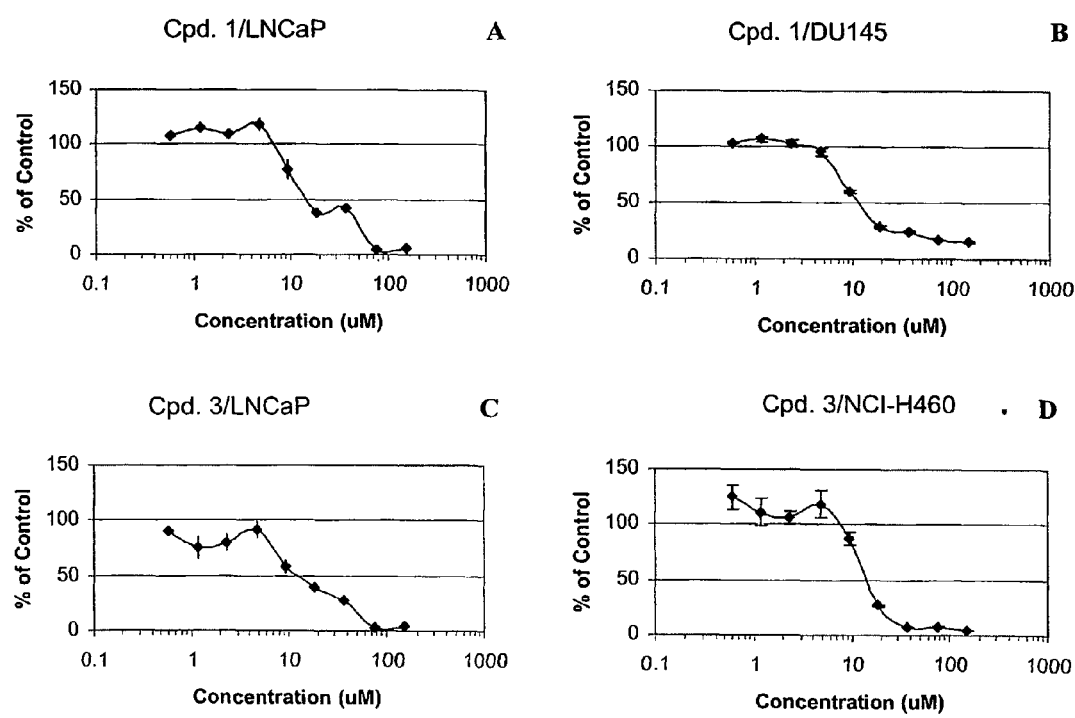
FIG. 1 represents cytotoxicity curves for Cpd. 1 and Cpd. 3 against selected tumor lines LNCaP, DU145 and NCI-H460 as follows.

Cytotoxicity Analysis:

Cpd. 1 and Cpd. 3 exhibited moderate anticancer activity with Cpd. 1 demonstrating activity against the prostate cancer lines LNCaP and DU-145 (FIGS. 1A and 1B; Table 1). A slightly better IC50 was observed against the androgen-independent prostate cancer line DU-145 (13.81 µM) when compared with LNCAP (16.25 µM), which is androgen responsive. Modest activity (>20 µM) was also observed against the other cell lines tested. Like Cpd. 1, Cpd. 3 also exhibited moderate activity against LNCaP (16.26 µM) (FIG. 1C; Table 1.), however while demonstrating some efficacy against DU-145 (19.2 µM), Cpd. 3 had activity against the large cell lung carcinoma line NCI-H460 (13.3 µM) (FIG. 1D and Table 1). Cpd. 3 had the best overall cell killing activity against all cell lines tested. In contrast to Cpd. 3, Cpd. 2, which has a nitro group instead of the methyl group in position 4 of the phenyl ring, had the lowest activity against all cell lines tested (Table 1).

Androgen Inhibition Studies:

In both studies investigating testosterone-induced proliferation of LNCaP cells a two-four fold induction was observed in the rate of growth of these cells in response to testosterone (FIGS. 2A and B). This testosterone-induced proliferation was potently blocked by finasteride (1 µM) (FIGS. 2A and B). Taken together these data demonstrate that the screening model is functioning. Of the 3 analogues tested, Cpd. 1 was the least potent (2.25 µM) inhibitor of testosterone-induced proliferation, while Cpd. 3 exhibited a 3 fold better result (IC50 0.68 µM) over Cpd. 1 (FIGS. 2, 3 and Table 2). Cpd. 2 was the most effective analogue at inhibiting testosterone-induced proliferation, with no IC50 determined at 37 nM, which is some 60-fold more effect than Cpd. 1 (FIGS. 2, 3 and Table 2). It is noted that Cpd. 2 having an electron-withdrawing group ($-NO_2$) in position 4 in comparison with an electron-donating group ($-CH_3$) (Cpd. 3) enhances the inhibitory activity of the molecule in this particular assay.

Example 3

Results and Discussions

Inhibition of Thromboxane Synthase and COX:

Cpd. 1 and Cpd. 3 exhibited 100% inhibition of COX activity when assayed at 10 µM, while Cpd. 2 inhibited this activity by 77% (FIG. 4). Likewise, 10 µM Cpd. 1, Cpd. 2 and Cpd. 3 inhibited thromboxane synthase by 33, 27 and 60% respectively but their inhibitory effect was less potent in comparison with their inhibition of COX. These data support the finding that the aminated isoflavone analogues are inhibitors of thromboxane synthase and COX and as such, molecules with this scaffold exhibit potential as anti-inflammatory agents. In addition, therapeutic application as NSAIDS inhibition of COX activity supports that the phenylhydrazone analogues also exhibit anti-cancer activity.

Cpd. 3 and Cpd. 1 were found to be the more effective anticancer agents with respect to their direct killing ability, however, they were less effective at inhibiting testosterone-induced proliferation. The most effective analogue inhibiting testosterone-induced proliferation was Cpd. 2, which was the least effective analogue in the direct cell-killing assay. These results show that there are variations on the activities and modes of action in the two anti-cancer screens the test compounds were subjected to. Further, the ability of these aminated analogues to inhibit COX confirms that this class of molecule has multiple anti-cancer applications and their ability to inhibit thromboxane synthase suggests a role in anti-inflammation.

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited herein, if any, are hereby incorporated by reference.

Those skilled in the art will appreciate that the invention described herein is susceptible to variations and modifica-

TABLE 1

Cytotoxicity comparison of Cpd. 1, Cpd. 2 and Cpd. 3 against PC3 (AR negative prostate Ca), LNCaP (AR positive Prostate Ca), DU145 (AR negative prostate Ca), MDA-MB-468 (ER negative breast Ca) and NCI-H460 (large cell lung Ca)

| | Cell Line (uM) | | | | | | | | | |
|---|---|---|---|---|---|---|---|---|---|---|
| | PC3 | | LNCaP | | DU-145 | | MDA-MB-468 | | NCI-H460 | |
| Analogue | Avg. | St. dev | Avg. | St. dev | Avg. | St. dev | Avg. | St. dev | Avg. | St. dev |
| Cpd. 1 | 33.9 | 2.26 | 16.2 | .074 | 13.8 | 2.12 | 34.9 | 19.3 | 27.6 | 0.60 |
| Cpd. 2 | 44.8 | 3.39 | 50.9 | 4.66 | 46.0 | 0.74 | 26.1 | 1.20 | 32.7 | 0.30 |
| Cpd. 3 | 27.9 | 6.43 | 16.2 | 3.88 | 19.1 | 1.62 | 22.4 | 5.52 | 13.3 | 1.62 |

TABLE 2

Phenylhydrazone analogue inhibition profile of testosterone-induced LNCaP proliferation

| Analogue | IC50 (uM) |
|---|---|
| Cpd. 1 | 2.25 |
| Cpd. 2 | ND @ 0.035 |
| Cpd. 3 | 0.68 | tions other than those specifically described. It is to be understood that the invention includes all such variations and modifications. The invention also includes all of the steps, features, compositions and compounds referred to or indicated in this specification individually or collectively, and any and all combinations of any two or more of said steps or features.

The reference to any prior art in this specification is not, and should not be taken as, an acknowledgment or any form of suggestion that that prior art forms part of the common general knowledge in the field of endeavour.

REFERENCES

Alley M C, Scudiero D A, Monks A, Hursey M L, Czerwinski M J, Fine D L, Abbott B J, Mayo J G, Shoemaker R H, Boyd M R. 1988 Feasibility of drug screening with panels of human tumor cell lines using a microculture tetrazolium assay. Cancer Res. 48: 589-601.

Amanatullah D F, Reutens A T, Zafonte B T, Fu M, Mani S, Pestell R G. 2000 Cell-cycle dysregulation and the molecular mechanisms of prostate cancer. Front. Biosci., 5: D372-90.

Chen G S, Chang C S, Kan W M, Chang C L, Wang K C, Chern J W 2001 Novel lead generation through hypothetical pharmacophore three-dimensional database searching: discovery of isoflavonoids as nonsteroidal inhibitors of rat 5 alpha-reductase. J Med Chem 44, 3759-63.

Hsing A W, Tsao L, Devesa S S. 2000 International trends and patterns of prostate cancer incidence and mortality. Int. J. Cancer 85, 60-7.

Fosslien, E. 2001 Molecular pathology of COX-2 in cancer-induced angiogenesis. Ann. Clin. Lab. Science. 31, 325-348.

Koki, A. T. and Masferrer, J. L. 2002 Celecoxib: A specific COX-2 Inhibitor with anticancer properties. Cancer Control 9, Supp. 28-35.

Landis S H, Murray T, Bolden S, Wingo P A. 1999 CA Cancer J. Clin. 49, 8-31.

Morris, M. J. and Scher, H. I 2000 Novel strategies and therapeutics for the treatment of prostate carcinoma. Cancer 89, 1329-1348.

Negri-Cesi, P., Motta, M., 1994 Androgen metabolism in the human prostatic cancer cell line LNCaP. 1994 J. Steroid Biochem. Molec. Biol. 51, 89-96.

Negri-Cesi, P., Colciago, A., Poletti, A. and Motta, M. 1999 5a-Reductase isozymes and aromatase are differentially expressed and active in the androgen-independent human prostate cancer cell lines DU145 and PC3. The Prostate 41, 224-232.

Papatsoris, A. G and Papavassiliou, A. G. 2001 Prostate cancer: horizons in the development of novel anti-cancer strategies. Curr. Med. Chem.—Anti-cancer agents. 1, 47-70.

Penglis, P. S., Cleland, L. G., Demasi, M., Caughey, G. E. and James, M. J. 2000. Differential regulation of prostaglandin E2 and thromboxane A2 production in human monocytes: implications for the use of COX inhibitors. J. Immunol. 165, 1605-11.

Vaino, H. 2001 Is Cox inhibition a panacea for cancer prevention. Int. J. Cancer 94, 613-614.

The invention claimed is:

1. A compound of formula (III) or (VIII):

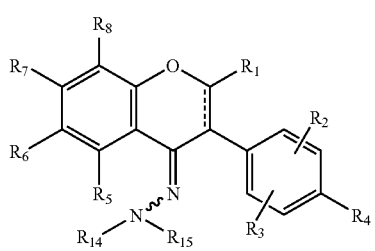

(III)

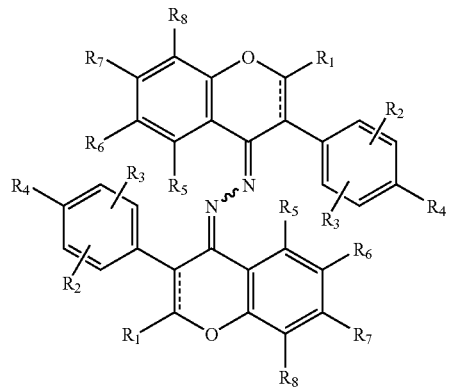

(VIII)

wherein
$R_1$ is hydrogen,
$R_2$, $R_3$ and $R_4$ are independently hydrogen, hydroxy or $OR_9$,
$R_7$ is hydroxy,
$R_5$, $R_6$ and $R_8$ are independently hydrogen, hydroxy, or $C_{1-6}$ alkyl,
$R_9$ is $C_{1-6}$ alkyl,
one of $R_{14}$ and $R_{15}$ is hydrogen,
the other one of $R_{14}$ and $R_{15}$ is hydrogen or is phenyl, benzyl, or pyridyl optionally substituted by one of $C_{1-4}$ alkyl, nitro, $OR_9$, halo or cyano, and
the drawing "---" represents either a single bond or a double bond,
or a pharmaceutically acceptable salt thereof.

2. A compound according to claim 1, wherein
$R_2$, $R_3$, and $R_4$ are independently hydrogen, hydroxyl, or methoxy,
$R_5$ and $R_6$ are hydrogen,
$R_8$ is hydrogen or $C_{1-6}$ alkyl, and
the other one of $R_{14}$ and $R_{15}$ is hydrogen or is phenyl, benzyl or pyridyl optionally substituted by one of methyl, nitro, methoxy, chloro or cyano,
or a pharmaceutically acceptable salt thereof.

3. A compound according to claim 2, wherein
$R_2$ and $R_3$ are hydrogen, $R_4$ is hydroxy or methoxy,
$R_8$ is hydrogen or methyl,
$R_{14}$ is hydrogen and $R_{15}$ is phenyl optionally substituted by one of methyl, nitro, methoxy, chloro or cyano, and
the drawing "---" represents a single bond,
or a pharmaceutically acceptable salt thereof.

4. A compound according to claim 3 selected from compounds (1)-(10):
4',7-Dihydroxyisoflavanone (phenyl)hydrazone (1)
4',7-Dihydroxyisoflavanone (4-nitrophenyl)hydrazone (2)
4,7-Dihydroxyisoflavanone (4-methylphenyl)hydrazone (3)
4',7-Dihydroxyisoflavanone (benzyl)hydrazone (4)
4,7-Dihydroxyisoflavanone(4,7-dihydroxyisoflavanone) hydrazone (5)
4',7-Dihydroxyisoflavanone (2-chlorophenyl)hydrazone (6)
4',7-Dihydroxyisoflavanone (3-chlorophenyl)hydrazone (7)
4',7-Dihydroxyisoflavanone (4-chlorophenyl)hydrazone (8)
4',7-Dihydroxyisoflavanone (2-pyridyl)hydrazone (9)

4',7-Dihydroxyisoflavanone (4-cyanophenyl)hydrazone (10)

or a pharmaceutically acceptable salt thereof.

5. A process for the preparation of a compound of formula (III) or (VIII) as defined in claim 1 comprising the step of reacting the 4-keto group of a compound of the formula (X):

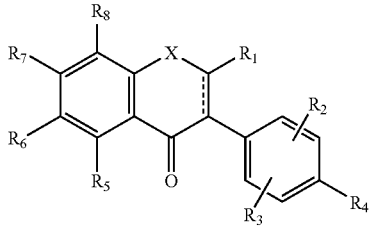

wherein
$R_1, R_2, R_3, R_4, R_5, R_6, R_7$ and $R_8$ are as defined in claim 2,
X is O, and
the drawing "---" represents either a single bond or a double bond, with a hydrazine aminating agent of formula $H_2N-NR_{14}R_{15}$,
wherein one of $R_{14}$ and $R_{15}$ is hydrogen, and
the other one of $R_{14}$ and $R_{15}$ is hydrogen or is phenyl, benzyl, or pyridyl optionally substituted by one of $C_{1-4}$ alkyl, nitro, $OR_9$, halo or cyano.

6. A pharmaceutical composition which comprises one or more compounds of formula (III) or (VIII) as defined in claim 1 or a pharmaceutically acceptable salt thereof in association with one or more pharmaceutical carriers, excipients, auxiliaries and/or diluents.

7. A drink or food-stuff, which contains one or more compounds of formula (III) or (VIII) as defined in claim 1 or a pharmaceutically acceptable salt thereof.

8. A compound selected from:
4',7-Dihydroxy-4-methylimino-isoflavan (11)
4',7-Dihydroxyisoflavanone oxime (12)
4-Amino-3',4'-dimethoxy-7-hydroxy-8-methylisoflavan (13)
N-(3',4'-dimethoxy-7-hydroxy-8-methyl-4-chromanyl)-acetamide (14)
and pharmaceutically acceptable salts thereof.

* * * * *